United States Patent [19]

Nunn et al.

[11] 4,427,013

[45] Jan. 24, 1984

[54] APPARATUS AND METHOD FOR MEASURING BLOOD PRESSURE

[75] Inventors: Donald E. Nunn, Glendora; Robert W. Beveridge, Cosa Mesa, both of Calif.

[73] Assignee: C.R. Bard, Inc., Murray Hill, N.J.

[21] Appl. No.: 502,151

[22] Filed: Jun. 8, 1983

Related U.S. Application Data

[63] Continuation of Ser. No. 229,320, Jan. 29, 1981, abandoned.

[51] Int. Cl.³ ................................................ A61B 5/02
[52] U.S. Cl. .................................................. 128/681
[58] Field of Search ................ 128/680, 681, 682, 670

[56] References Cited

U.S. PATENT DOCUMENTS

| | | | |
|---|---|---|---|
| 3,315,662 | 4/1967 | Buffington | 128/681 |
| 4,009,709 | 3/1977 | Link et al. | 128/683 |
| 4,105,021 | 8/1978 | Williams et al. | 128/681 |
| 4,154,238 | 5/1979 | Link | 128/681 |
| 4,263,918 | 4/1981 | Swearingen et al. | 128/681 |
| 4,271,843 | 6/1981 | Flynn | 128/681 |

OTHER PUBLICATIONS

Yeldermame Ream, "A Microprocessor Based Automated Non-Invasive Blood Pressure . . . ", Proc. 17th Ann. San Diego Bio. Med. Sym. 1978.
Ramsey— "Non-Invasive Automatic Determination of MAP", Med. & Bio. Eng. & Comp. 1979, vol. 17, pp. 11-18.
Looney, "Blood Pressure by Oscillometry", Med. Electronics, Apr. 1978.
Link, "The Norse Systems Automatic Electronic Blood Pressure Monitor Using Waveform Analysis Oscillometry", Internal Document Noise Inc.

*Primary Examiner*—William Kamm
*Assistant Examiner*—Mitchell J. Shein
*Attorney, Agent, or Firm*—Wolf, Greenfield & Sacks

[57] ABSTRACT

A blood pressure measuring device is disclosed which uses an inflatable cuff to apply external pressure to a patient's body member. The device detects and measures amplitude of pressure oscillations induced in the cuff by blood flow in the body member as the cuff pressure is decreased in steps from a magnitude above the expected systolic pressure to a magnitude below the expected diastolic blood pressure. The means arterial blood pressure is measured at the step at which the pressure oscillations reach a maximum. Systolic blood pressure is determined by making a first linear approximation to a plurality of amplitude measurements occurring below the expected systolic pressure and making a second linear approximation to a plurality of points occurring above the expected systolic pressure. The systolic pressure is calculated by setting the two approximations equal. Diastolic blood pressure is determined by detecting the cuff pressure which results in an equivalent oscillation magnitude to that determined for the systolic pressure.

15 Claims, 4 Drawing Figures

APPARATUS AND METHOD FOR MEASURING BLOOD PRESSURE

This application is a continuation of application Ser. No. 229,320, filed Jan. 29, 1981, now abandoned.

FIELD OF THE INVENTION

This invention relates in general to blood pressure measuring apparatus and, in particular, to blood pressure measuring devices which measure arterial blood pressure by oscillometry—the monitoring of pressure oscillations produced by arterial blood pulsations within a pressurized air cuff.

BACKGROUND OF THE INVENTION

The variations of blood pressure occurring during various physiological states of a patient is of great interest in modern medical diagnostic procedures. The traditional method of characterizing blood pressure is a determination of the systolic and diastolic pressure values. Another measurement variable, the mean arterial pressure (MAP), has also been determined to be useful as an indication of blood pressure. The mean arterial blood pressure is defined as the time average of the instantaneous blood pressure or as a weighted average of the systolic and diastolic pressures. In particular, if blood pressure is plotted relative to time, the MAP is a level chosen so that the area between the systolic section of the curve and the MAP level equals the area between the MAP level and the diastolic section of the curve. The MAP level can be roughly estimated from the systolic and diastolic values according to the following formula:

$$MAP = Diastolic + \tfrac{1}{3}(Systolic - Diastolic)$$

The value determined by this equation may be inaccurate in shock cases, in an operating room environment, or where certain diseases are involved due to changes in the blood pulse waveform.

There are presently several methods of measuring the various values of arterial blood pressure which are in common use. The most accurate method is direct measurement of arterial pressure by using an arterial cannula. However, invasive techniques are often inconvenient and may give rise to considerable patient discomfort.

Accordingly, several noninvasive techniques have been developed. One of the earliest techniques which is in common use involves occluding the blood vessels in a patient's limb by means of inflatable cuff which encircles the limb. The pressure (typically, air) in the cuff is then slowly decreased. When the decreasing pressure equals the arterial systolic pressure, characteristic sounds commonly known as Korotkoff sounds can be heard by auditory monitoring of the blood flow. When the decreasing pressure in the cuff reaches the arterial diastolic pressure, the Korotkoff sounds also change in a characteristic manner. These phenomena can be easily used to measure the systolic and diastolic blood pressure by observing the cuff pressure by means of conventional mercury or aneroid spnygmomanometer while manually listening to the blood flow in the arteries. The technique has also been automated by detecting the Korotkoff sounds using microphones or ultrasound transducers in the inflatable cuff. One problem with this method is that it cannot be used to directly measure the mean arterial pressure which must be estimated from the systolic and diastolic values using the formula referred to above. This formula may be inaccurate due to a variety of factors including disease or shock.

A more recently discovered technique is the oscillometric method of detecting and quantifying blood pressure values. This technique utilizes a blood vessel-occluding air cuff as in the Korotkoff technique, but senses blood pressure values by a different means. Specifically, as the air pressure in the inflatable air cuff is decreased below the systolic blood pressure, small pressure oscillations can be observed above the baseline cuff pressure. These small pressure oscillations are reflected in the air pressure of the surrounding cuff as result of expansion and contraction of the arteries produced by the pulsatile blood flow. The pressure oscillations increase in amplitude and reach a maximum as the cuff pressure becomes equal to the mean arterial blood pressure. The oscillations then decrease in amplitude until they entirely disappear below a threshold value of the applied cuff-pressure. The mean arterial pressure is then easily measured by detecting the air cuff pressure at which the maximum amplitude of the pressure oscillations in the air cuff occurs. This measurement technique is easily automated and is especially useful in blood pressure and measuring devices that are controlled by microprocessors.

However, one problem with prior art blood pressure measuring devices using the oscillometric method is that although the mean arterial pressure can easily be measured, no simple, accurate method for measuring either systolic or diastolic pressures has been developed.

Consequently, most prior art devices rely on an extrapolation of the systolic and diastolic pressures from the measured mean arterial pressure. For example, it has been observed that the systolic and diastolic pressures occur at points where the pressure oscillations in the air cuff reach a magnitude which is approximately one half the magnitude of the oscillations at the mean arterial pressure. This method provides an easy way of calculating the systolic and diastolic pressures from the mean arterial pressure. However, it is subject to several additional problems. First, artifacts introduced by patient movement or outside interference may produce erroneous results if they occur at cuff pressure measurements in the vicinity of the diastolic or systolic pressures. Secondly, the one-half magnitude relation of the oscillation amplitudes at mean pressure and systolic/diastolic pressures is not exactly correct. Therefore the systolic and diastolic pressures calculated by this technique are only approximations as to the true systolic and diastolic pressures.

Accordingly, it is an object of the invention to provide a more accurate method for determining systolic and diastolic blood pressure values in an oscillometric-mode blood-pressure measuing system.

It is another object of the invention to obtain accurate systolic and diastolic blood pressure readings in the presence of noise and other external disturbances and in the case of shock, operating room environments and disease situations.

It is a further object of the invention to obtain increased artifact rejection in obtaining systolic and diastolic blood pressure readings.

SUMMARY OF THE INVENTION

The above problems are solved and the objects accomplished in an illustrative embodiment of the invention in which a more accurate determination of systolic and diastolic pressure values is produced and erroneous results which might be produced by artifacts are avoided by calculating the systolic and diastolic pressures from a series of measurements taken at cuff pressures in the region of the systolic and/or the diastolic pressure rather than from just a single measurement of the mean arterial pressure or from a single measurement taken in the vicinity of the systolic or the diastolic pressure.

Specifically, it has been determined that as the cuff air pressure in the blood vessel-occluding (air) cuff is decreased from a value above the systolic blood pressure, the oscillations which occur in the cuff air pressure slowly increase in amplitude at a gradual and a first approximately constant rate. However, when the cuff air pressure reaches the vicinity of the systolic pressure the rate of increase of the oscillation magnitudes sharply increases. The oscillation magnitudes then continue to grow at approximately the second constant increased rate as the cuff air pressure is decreased, until the mean arterial pressure is reached and the maximum amplitude of oscillation occurs. The oscillation magnitudes then decrease at approximately the same rate as the second increased rate until the diastolic pressure is reached. At this point the rate of decrease of oscillation magnitudes changes to a second more gradual rate until a cuff pressure is reached at which the oscillations disappear. The present invention determines the systolic pressure by determining the cuff pressure at which there is a change in the rate of increase of the oscillation magnitudes as the cuff pressure is passing through the pressure corresponding to the systolic pressure. The diastolic pressure is then determined by measuring the cuff air pressure at an oscillation magnitude corresponding to the oscillation magnitude at the measured systolic pressure.

Specifically, in an illustrative embodiment of the invention, a series of "readings" are taken as the cuff pressure is decreased. Each reading consists of the peak oscillation magnitude and the corresponding baseline cuff air pressure. A plurality of magnitude readings are selected which occur at respective cuff pressures above the expected systolic pressure. In addition, a plurality of magnitude readings are selected which occur at respective cuff pressures below the expected systolic pressure. Two relationships representing, respectively, the change of the peak amplitudes of each set of readings with the change of the cuff pressure, are derived by well-known methods from each set of readings. The relationships, which, for example, may be straight line equations, are manipulated to determine values of cuff pressure and corresponding oscillation magnitudes which satisfy both relationships; in a mathematical sense, they are set equal and solved for the systolic pressure. In a graphical sense, the two functions represent curves (illustratively straight lines) connecting the peak values of each set); such curves extended, *intersect* at a cuff pressure value equal to the systolic pressure.

The diastolic presssure is subsequently determined by detecting a cuff pressure amplitude which produced an oscillation magnitude equal to the oscillation magnitude at the calculated systolic pressure. It will be appreciated that this procedure could be reversed; the diastolic pressure can be determined first, and the systolic pressure can then be determined from it.

DETAILED DESCRIPTION

Figure 1:
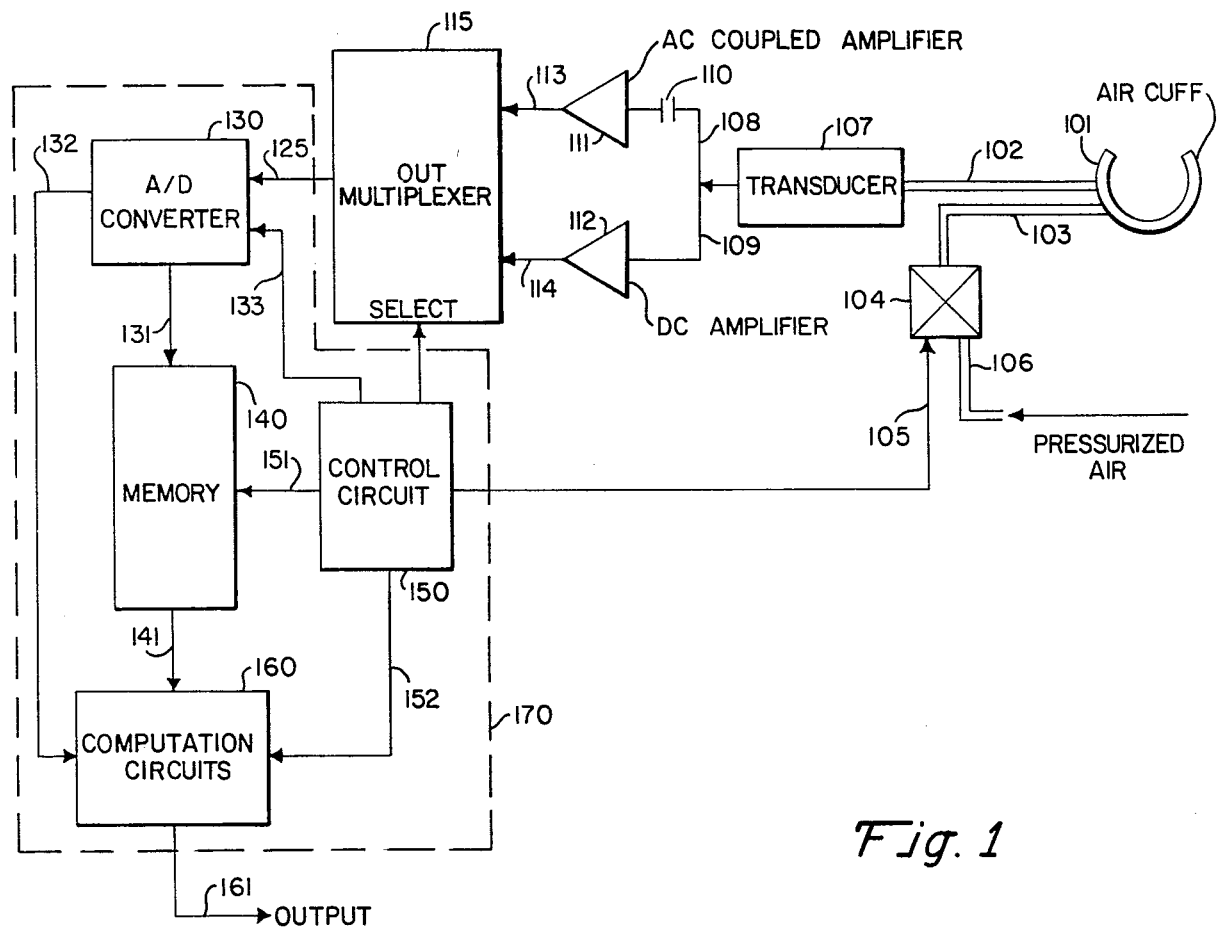
FIG. 1 shows a block schematic diagram of an illustrative blood pressure measuring device suitable for use with the invention.

Referring to FIG. 1, an air cuff 101 is placed around the limp of a patient, preferrably on the upper arm or upper leg in order to controllably occlude the blood vessels in preparation for the measurement of the arterial blood pressure. Cuff 101 is a well-known device which typically contains an air bladder that has two flexible tubing connections 102 and 103. The air bladder in cuff 101 may be inflated or deflated by means of flexible tube 103 which is connected to valve 104. Valve 104 is controlled, via lead 105, by control circuit 150 as will be hereinafter described and operates to inflate cuff 101 by means of pressurized air which is provided from a compressed air source (not shown) through tube 106. Valve 104 may also operate under control of control circuit 150 to release air pressure from cuff 101 in graduated steps. The air bladder in cuff 101 is also provided with a second flexible connection 102 which is attached to a transducer unit 107. The second connection allows measurements to be made on the air pressure in the cuff without interference from the air flow on the tube 103. Transducer unit 107 responds to the air pressure in the cuff relative to atmospheric pressure and produces an electronic signal. The magnitude of the electronic signal is proportional to the pressure in cuff 101. The output of transducer 107 is provided via leads 108 and 109 to amplifiers 111 and 112. Amplifier 112 is a D.C. amplifier which produces at its output 114 a signal that is representative of the average baseline pressure in cuff 101. Amplifier 111 is an A.C. coupled amplifier (shown schematically as amplifier 111 in a series connection with capacitor 110) which produces a signal at its output 113 in response to the oscillations in pressure that result from the pulsation of the blood vessels within the patient's limb. Either ouput 113 of amplifier 111 or output 114 of amplifier 112 can be selected by multiplexer 115 under control of control circuit 150, via lead 120, and applied, via lead 125, to analog-to-digital converter 130. Converter 130 converts the analog signals produced by amplifiers 111 and 112 to digital signals which are used by the processing circuitry in order to compute the mean arterial, systolic and diastolic blood pressures.

Therefore, in summary, control circuit 150 may operate multiplexer 115 and analog-to-digital converter 130 to produce a digital signal which is representative of the baseline pressure in air cuff 101, via amplifier 112, or the amplitude of the pressure oscillation in air cuff 101 produced by the blood flow in the patient's blood vessels, via amplifier 111.

As will be hereinafter be described in further detail control circuit 150 operates memory 140 and computation circuit 160 to selectively make a plurality of readings, each reading consisting of a baseline pressure and corresponding oscillation magnitude. After completing a plurality of such readings, control circuit 150 operates memory 140 to transfer selected readings to computation circuit 160, via channel 141. Control circuit 150 then operates in conjunction with computation circuit 160 to compute the mean, systolic and diastolic blood pressures which are produced on output 161.

In the illustrative embodiment described herein, analog-to-digital converter 130, memory 140, control circuit 150 and computation circuit 160 (all as shown in the enclosed dotted box 170) may be implemented as a microprocessor. Alternatively, conventional circuitry may be used to implement the functions which will be hereinafter described.

Figure 2:
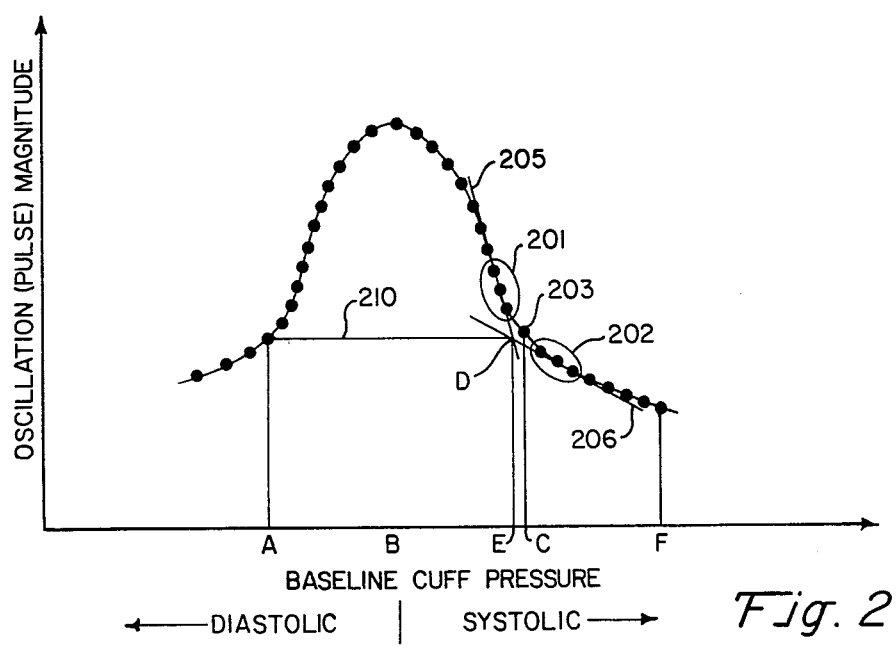
FIG. 2 shows a typical set of readings taken by means of the apparatus in FIG. 1.

FIG. 2 shows a typical set of readings which are taken by means of the circuitry shown in FIG. 1. The Figure consists of a graph in which the horizontal axis represents baseline cuff pressure increasing towards the right and the vertical axis represents oscillation magnitude increasing in the upward direction. The series of dots or "points" on the graph each represent a single reading which has corresponding oscillation magnitude and baseline cuff pressure as read on the horizontal and vertical axis. FIG. 2 will be used in connection with FIGS. 3 and 4 to describe the operation cycle of the circuitry disclosed in FIG. 1.

Figure 3:
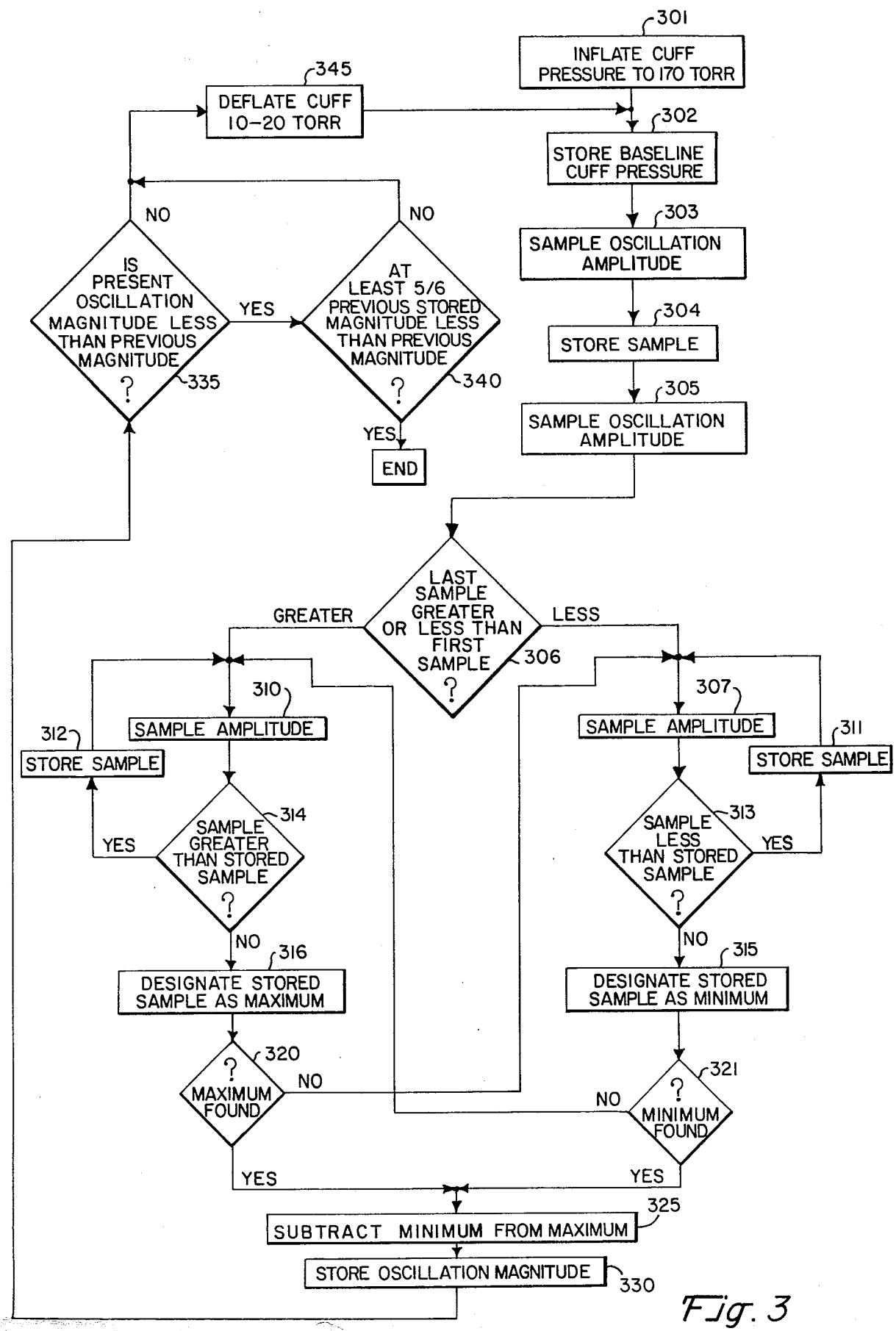
FIG. 3 is a flow diagram of the operation of the circuitry shown in FIG. 1 used to take the readings shown in FIG. 2.

Specifically, in FIG. 3, the flow diagram illustrates the operation of the circuitry in FIG. 1 during the taking of data readings on the pressure signals produced by air cuff 101. In step 301, control circuit 150 operates valve 104 to inflate air cuff 101 to a pressure which is higher than the expected systolic pressure. In the illustrative embodiment cuff 101 is inflated to 170 Torr.

In step 302, control circuit 150 causes the output signal of analog-to-digital convertor 130 representative of the baseline cuff pressure to be stored in memory 140. In step 303, control circuit 150 causes a sample of the oscillation amplitude (in digital form) produced by a convertor 130 to be stored in memory 140. Typically, oscillations occur in the air pressure in cuff 101 at the frequency of the patient's pulse rate which is typically 60 to 80 Hertz. The sampling operation on the amplitude, however, is conducted at a much higher frequency so that the variation in the oscillation amplitude during the sample period is minimal. In step 304 the sampled amplitude from the output of convertor 130 is stored in memory 140.

In step 305, the oscillation amplitude is sampled again. This sampling operation takes place at predetermined intervals. In step 306, the two samples previously obtained are compared. If the second sample is less than the first, step 307 is executed. If the second sample greater than the first, step 310 is executed. Assuming that the second sample is less, in step 307, control circuit 150 takes an additional sample of the oscillation amplitude and compares it (in step 313) to the sample previously stored in memory 140. If the present sample is less than the stored sample (indicating that the oscillation magnitude is still decreasing) the most recent sample is stored in place of the previous stored sample (step 311) and a new sample is taken (step 307). This operation is continued until a present sample is greater than the stored sample indicating that the minimum of the oscillation magnitude has been reached. In this case control circuit 150 executes step 315 and designates the stored sample as a minimum.

Control circuit 150 then determines whether a maximum value of the oscillation amplitude has been determined at step 321. If not, steps 310, 312, 314, and 316 are executed in which additional samples are taken and compared to a previously stored sample until a present sample is less than the stored sample indicating a maximum has been found. When this occurs the maximum is designated in step 316. Since a minimum has already been found in step 320, control circuit 150 progresses to step 325 in which the minimum value is subtracted from the maximum value to generate the peak-to-peak magnitude of the oscillation. This value is stored in step 330 and control circuit 150 then compares the present oscillation magnitude stored in step 330 to those previously stored to determine whether the oscillation magnitude is increasing or decreasing.

Assuming that the oscillation magnitude is increasing (indicating that the mean arterial pressure has not been reached yet) step 345 is executed in which the air pressure in cuff 101 is deflated by a predetermined amount. This amount may illustratively be in the range of 10 to 20 Torr. A new set of readings is taken and operation in this manner continues until, in step 335, it is determined that the present oscillation magnitude is less than the previous magnitude. In this case control circuit 150 executes step 340 and determines whether at least five out of the six previous stored magnitudes are greater than the present magnitude. If this condition is satisfied it indicates that the baseline cuff pressure has passed through the diastolic pressure point and that measurements may be discontinued. If this condition is not satisfied, operation is continued until the baseline pressure does pass through the diastolic point.

When the end of the operation shown in flow chart 3 has been reached, a series of readings consisting of pairs of measured points will have been stored in memory 140. If plotted on graph paper these points would appear as shown in FIG. 2. Before proceeding to a specific description of the calculation of the systolic and diastolic blood pressures the specific characteristics of the readings shown in FIG. 2 will be discussed. When plotted as in FIG. 2, the readings assume a "bell-shaped" curve. As is well-known in the art, the baseline cuff pressure corresponding to the maximum of the curve (point B) is equivalent to the mean arterial blood pressure. The systolic and diastolic pressure points occur where the oscillation magnitude decreases to approximately half its value at the maximum. At this point, for example, in the vicinity of points A and C the slope of the curve exhibits a marked change or "breakpoint", (which is exaggerated in the figure to clarify the description).

In accordance with the present invention, a calculation of the breakpoint 203 in the slope of the curve is made using additional data points in the vicinity of the expected systolic pressure in order to achieve an accurate calculation of the systolic pressure. Specifically, a reading is chosen as a starting point in which the oscillation magnitude is approximately one half of the peak amplitude. This would correspond to point 203 in FIG. 2. Two sets of three readings each are taken around point 203 corresponding to three readings with the baseline cuff pressure greater than the pressure at point 203 and three readings with the baseline cuff pressure less than the cuff pressure at point 203. In the illustrative embodiments these groups are chosen as 201 and 202 respectively. Using the three points contained in group 201, a straight line approximation (shown in 205) to the curve is made using standard mathematical procedures. Similarly, a straight line approximation (206) is made using the three points in group 202. The pressure corresponding to the intersection of the two straight lines (point D) corresponding to cuff pressure E on FIG. 2, is the calculated systolic pressure. In order to calculate the diastolic pressure, a reading is chosen on the diastolic side of the curve in which the magnitude of the oscillations shown by line 210 is equivalent to that calculated for the systolic pressure. The corresponding baseline cuff pressure (shown at point A) is the calculated diastolic pressure.

As will be appreciated, these measurements can be performed by hand, using a graph plotted from measurements taken by the apparatus, so as to reproduce FIG. 2, and constructing the straight lines 205 and 206 on the graph.

Figure 4:
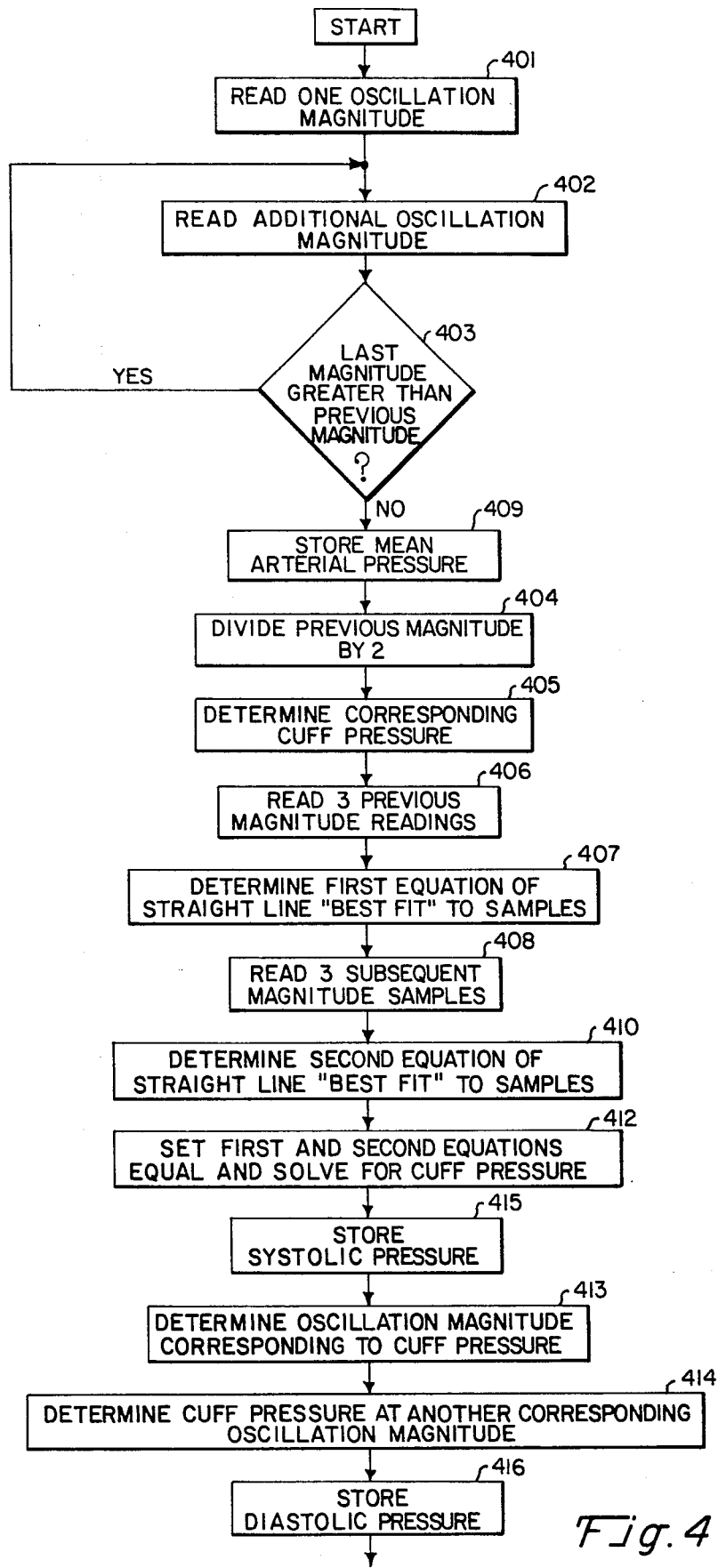
FIG. 4 is a flow diagram of the routine used to calculate the systolic and diastolic pressures.

In FIG. 4, the operations performed by the circuitry shown in FIG. 1 in order to calculate the mean, systolic and diastolic pressures are shown.

After obtaining and storing readings corresponding to baseline cuff pressures in a range including the expected systolic and diastolic pressures as described above, control circuit 150 selects two readings corresponding to the highest baseline cuff pressure and the next to highest baseline cuff pressure (readings 215 and 220 respectively in FIG. 2). The magnitude of the oscillations in the two readings are compared in step 403. If the magnitude read last is greater than the magnitude read immediately before, step 402 is repeated and an additional magnitude is read and compared to the one which was just previously read. This process is repeated until the present magnitude reading is less than the previous magnitude reading. This occurs at point B in FIG. 2 corresponding to the mean arterial pressure.

In order to select a starting point for the systolic pressure calculation, the value of the oscillation magnitude at the mean arterial pressure point (B in FIG. 2) is divided by two in step 404. In step 405, the corresponding cuff pressure is determined. This would correspond to point 203 and pressure C in FIG. 2. Having determined the starting point for the systolic pressure determination, control circuit 150 then reads from memory 140 the oscillation magnitudes and baseline pressure values of a plurality of readings which were made previous to the reading 203. In the illustrative embodiment, three readings are selected. These would correspond to the readings at points 202 in FIG. 2. The values are read into computation circuit 160. Under control of control circuit 150, computation circuit 160 determines a a mathematical relationship which best "fits" the plurality of points read from memory 140. Illustratively, the relationship may be a straight line equation.

The determination of such a straight line equation can be accomplished in any number of well-known mathematical techniques. Illustratively, as a simple approximation, one of the three readings may be assumed to coincide with the mathematical averages of the three readings. The sum of the errors is then minimized, resulting in a line with a slope that is the average of the slopes of two lines passing through each of the remaining readings and a point corresponding to the averages of the three readings. Using this method, an equation is derived from the readings which has the form.

$$O = CM + B.$$

where O is the oscillation magnitude, C is the baseline cuff pressure and M and B are constants equal to the slope of the line and the $\gamma$-axis intercept. Assuming, for the purposes of illustration, that the points in an illustrative group have the coordinates $O_1, C_1; O_2, C_2; O_3, C_3$, in accordance with the above approximation method the constants M and B are given by the following equations:

$$M = \frac{1}{2}\left[\frac{(O_1 - \overline{O})}{(C_1 - \overline{C})} + \frac{(O_3 - \overline{O})}{(C_3 - \overline{C})}\right]$$

and $$B = \overline{O} - \overline{C}M$$

Where $\overline{O}$ and $\overline{C}$ are simple averages of the point coordinates given by the following equations:

$$\overline{O} = \frac{O_1 + O_2 + O_3}{3}$$

$$\overline{C} = \frac{C_1 + C_2 + C_3}{3}$$

The well-known technique of "least squares" approximation may also be used. In accordance with the least squares method of straight line approximation, the slope of the derived equation is as follows:

$$M = \frac{(C_1 - \overline{C})(O_1 - \overline{O}) + (C_2 - \overline{C})(O_2 - \overline{O}) + (C_3 - \overline{C})(O_3 - \overline{O})}{(C_1 - \overline{C})^2 + (C_2 - \overline{C})^2 + (C_3 - \overline{C})^2}$$

Where $\overline{O}, \overline{C}$, and B are given by the previous equations. Utilizing either of these equations and the coordinates of the readings for the points in group 203, a straight line approximation of the form:

$$O_p = C_p M_p + B_p$$

is obtained. The subscript p indicates the coefficients $M_p$ and $B_p$ are for readings taken previous to the expected systtolic point 203.

After determining the value of the M and B coefficients for the first set of points, in step 408, control circuit 150 then reads from memory 140 the oscillation magnitude and corresponding baseline pressure values of the three readings taken subsequently to point 203 (corresponding to set 201 in FIG. 2). Using the readings thus obtained, in step 410, control circuit 150 determines a second equation of the best fit to the readings. As previously mentioned, an equation is obtained of the form:

$$O_s = C_s M_s + B_s$$

Where the subscript s indicates that the coefficients are determined for the set of readings taken subsequently to point 203.

In accordance with the teaching of the invention, the calculated systolic pressure appears at point D in FIG. 2 where the two lines determined by the best-fit equations intersect. This point, of course, occurs where the calculated oscillation magnitudes $O_p$ and $O_s$ are equal. (In addition, the two baseline cuff pressures will be equivalent at that point $-C_p = C_s = C_{systolic}$). To determine this point, the two calculated equations are set equal and solved for the common baseline cuff pressure.

The calculated systolic blood pressure is given by the following equation:

$$C_{systolic} = \frac{B_s - B_p}{M_p - M_s}$$

The calculated systolic pressure in FIG. 2 corresponds to point E. In step 415, the calculated systolic pressure is stored.

The determination of the systolic pressure in accordance with the method of the invention results in an accurate determination of the systolic value. Even if one of the readings used in the approximation should be erroneous due to patient movement or other external noise, a reasonable approximation can still be obtained. This operation is in contrast to prior-art methods, such as differentiation, which are quite sensitive to artifacts in the region of the systolic pressure. In extremely noisy conditions better noise and artifact rejection may be obtained by increasing the number of readings which are used to make the approximation.

In accordance with another aspect of the invention, the diastolic pressure is determined in accordance with step 414 by first determining the oscillation magnitude corresponding to the calculated systolic pressure. This can be easily determined by substituting the calculated systolic pressure value into either of the derived equations giving the corresponding oscillation magnitude $O_{systolic}$ as $$O_{systolic} = C_{systolic} M_s + B_s$$

Control circuit 150, in accordance with step 414, then searches through memory 140 for readings on the diastolic portion of the oscillation magnitude—cuff pressure curve to find the cuff pressure which corresponds to the oscillation magnitude calculated immediately above (point A in FIG. 2). In step 416 the calculated diastolic pressure is stored.

The stored systolic and diastolic pressures may be displayed in any suitable manner by means of digital or analog devices which are well-known to those skilled in the art.

Variations of the technique and apparatus disclosed herein within the spirit of the invention will be obvious to those skilled in the art. For example, the diastolic pressure may be calculated first by making two linear approximations to sets of points in the vicinity of the expected diastolic pressure and setting the approximations equal exactly in the manner disclosed herein for calculating the systolic pressure. The systolic pressure may then be derived by determining the cuff pressure at which the oscillation amplitude is equivalent in magnitude.

In addition, mathematical relationships other than straight line equations may be derived from the sets of readings according to well-known approximation techniques.

What is claimed is:

1. A non-invasive method for measuring systolic blood pressure in a body member, including the steps of:
   A. occluding blood flow in said body member by applying a variable and measurable external pressure to said member;
   B. varying said pressure between a magnitude whereat said blood flow is substantially occluded and a magnitude whereat said blood flow is substantially unoccluded;
   C. measuring, at a plurality of pressure values, the peak-to-peak oscillation magnitude of oscillations in said external pressure caused by blood flow pulses in said body member;
   D. storing a plurality of readings, each of said readings consisting of a pressure value and a corresponding oscillation magnitude, said stored readings forming a curve when plotted against each other;
   E. determining an expected value of said systolic blood pressure; and
   F. determining a selected pressure at or near said expected value at which the rate of change of the magnitude of said oscillations with respect to changes in said applied pressure undergoes a change.

2. A method according to claim 1 wherein step E comprises the steps of:
   E'. determining the maximum of said stored oscillation magnitudes; and
   E". determining said expected systolic pressure to occur at a pressure at which the corresponding oscillation magnitude is one-half said maximum oscillation magnitude.

3. A method according to claim 2 further comprising the steps of:
   G. forming a linear approximation to said curve for pressure values near but greater than said expected systolic blood pressure value;
   H. forming a linear approximation to said curve for pressure values near but less than said systolic blood pressure value; and
   I. selecting the pressure value at which both of said linear approximations yield the same oscillation magnitude.

4. A method according to claim 3 further comprising the steps of:
   J. determining the oscillation magnitude corresponding to said selected pressure; and
   K. determining an additional value of said pressure having a corresponding oscillation magnitude equal to said magnitude determined in step J, whereby said diastolic pressure is calculated.

5. Apparatus for measuring systolic blood pressure in a body member comprising:
   means for applying a variable and measurable external pressure to said member to occlude blood flow in said body member;
   means for varying said pressure between a magnitude whereat said blood flow is substantially unoccluded and a magnitude whereat said blood flow is substantially unoccluded;
   means for measuring the peak-to-peak oscillation magnitude at a plurality of pressure values;
   means for storing a plurality of readings, each of said readings consisting of a pressure value and a corresponding oscillation magnitude, said stored readings forming a curve when plotted;
   means for determining an expected value of said systolic blood pressure;
   means for determining the maximum pressure at which the rate of change of the magnitude of said oscillations with respect to changes in said applied pressure undergoes a change about said expected value.

6. Apparatus according to claim 5 further comprising:

means responsive to said maximum pressure and responsive to said output for determining the oscillation magnitude corresponding to said maximum pressure; and means responsive to values of said pressure and responsive said output for determining an additional value of said pressure having a corresponding oscillation magnitude equal to the output of said last-mentioned means whereby said diastolic pressure is calculated.

7. A non-invasive method for quantitatively determining one of the systolic blood pressure and the diastolic blood pressure for use with blood pressure measuring apparatus including means for applying a variable external pressure to an artery and means responsive to pulsatile waves occurring in a partially-occluded artery for detecting variations in said externally applied pressure, said method comprising the steps of:

A. imposing on said artery a time-varying external pressure extending over a pressure range including pressure equal to the expected systolic and diastolic blood pressures;

B. determining the peak amplitude of each pulsatile wave detected by said detecting means and determining the maximum of said peak amplitudes;

C. determining an expected systolic and an expected diastolic pressure to occur at pressures whereat the corresponding peak amplitude is one-half said maximum peak amplitude;

D. at a region of the external pressure range which includes one of the expected diastolic and systolic pressures determining a first rate of change with respect to said external pressure of the peak amplitudes of at least two waves occurring at external pressures near but in excess of said one expected pressure;

E. at said region, determining a second rate of change with respect to said external pressure of the peak amplitudes of at least two waves occurring at external pressures near but less than said one pressure; and F. quantitatively establishing said one pressure equal to that external pressure at which said first rate of change changes to said second rate of change.

8. A method according to claim 7 further comprising the steps of:

G. determining the peak amplitude corresponding to said one pressure; and

H. determining an additional value of said pressure having a corresponding peak amplitude equal to said peak amplitude determined in step G, whereby said other of said systolic and diastolic pressures is calculated.

9. A non-invasive method according to claim 7 wherein step B comprises the steps of:

B'. determining and storing the peak amplitude of each pulsatile wave detected by said detecting means as said external pressure varies between a magnitude greater than said expected systolic blood pressure and a magnitude lower than said expected systolic pressure and storing the the corresponding pressure value;

B''. determining from said stored peak amplitudes the maximum of said peak amplitudes.

10. A non-invasive method according to claim 9 wherein step D comprises the step of:

D'. determining from said stored peak amplitude values a first rate of change with respect to said external pressure of two or more successive and adjacent waves occurring at respective external pressure levels near but in excess of said one expected pressure;

and step E comprises the step of

E.' determining from said stored peak amplitude values a second rate of change with respect to said external pressure of the peak amplitudes of two or more successive and adjacent waves occurring at respective external pressure levels near but less than said one expected pressure.

11. A non-invasive method according to claim 10 wherein step D comprises the step of:

D'. determining from said stored amplitude values a first rate of change with respect to said external pressure of the peak amplitudes of three successive and adjacent waves occurring at respective external pressure levels near but in excess of the expected systolic pressure;

and step E comprises the step of

E.' determining from said stored peak amplitude values a second rate of change with respect to said external pressure of the peak amplitudes of three successive and adjacent waves occurring at respective external pressure levels near but less than the expected systolic pressure.

12. A non-invasive method for measuring systolic blood pressure in a body member, including the steps of:

A. occluding blood flow in said body member by applying a variable and measurable external pressure to said member;

B. varying said pressure between a magnitude whereat said blood flow is substantially occluded and a magnitude whereat said blood flow is substantially unoccluded;

C. monitoring the peak-to-peak magnitude of oscillations in said pressure produced by blood flow pulses in said body member;

D. storing a plurality of readings, each of said readings consisting of a pressure value and a corresponding oscillation magnitude, said stored readings, when plotted, forming a curve with at least one slope inflection point corresponding to the desired systolic blood pressure;

E. determining an expected value of said systolic blood pressure;

F. forming an approximation to said curve for pressure values near but greater than said expected systolic blood pressure value;

G. forming an approximation to said curve for pressure values near but less than said expected systolic blood pressure value; and H. determining the pressure value corresponding to said inflection point by selecting the pressure value at which both of said approximations yield the same oscillation magnitude to be the calculated value of said systolic pressure.

13. A method according to claim 12 wherein step E comprises the further steps of:

E'. determining the maximum of said oscillation magnitudes; and

E''. calculating the expected systolic pressure to occur at a pressure whereat the corresponding oscillation magnitude is one half said maximum oscillation magnitude.

14. A method according to claim 12 wherein the approximation in step F is a linear approximation.

15. A method according to claim 12 wherein the approximation in step G is a linear approximation.

* * * * *

UNITED STATES PATENT AND TRADEMARK OFFICE
CERTIFICATE OF CORRECTION

PATENT NO. : 4,427,013

DATED : January 24, 1984

INVENTOR(S) : Donald E. Nunn and Robert W. Beveridge

It is certified that error appears in the above—identified patent and that said Letters Patent is hereby corrected as shown below:

Column 10, lines 52 and 53, please change "unoccluded" to --occluded--.

Signed and Sealed this

Fourth Day of March 1986

[SEAL]

Attest:

DONALD J. QUIGG

Attesting Officer

Commissioner of Patents and Trademarks